United States Patent [19]

Farone

[11] 4,171,968

[45] Oct. 23, 1979

[54] METHOD FOR INCREASING THE RATE AND/OR YIELD OF SEED GERMINATION BY TREATMENT WITH SURFACTANTS

[75] Inventor: William A. Farone, Bon Air, Va.

[73] Assignee: Lever Brothers Company, New York, N.Y.

[21] Appl. No.: 807,101

[22] Filed: Jun. 16, 1977

[51] Int. Cl.$^2$ ............................................. A01N 21/02
[52] U.S. Cl. ....................................................... 71/77
[58] Field of Search ........................................... 71/77

[56] References Cited

U.S. PATENT DOCUMENTS

| 2,533,577 | 11/1946 | Hale et al. ............................... 71/77 |
| 2,689,173 | 9/1954 | Clarke ..................................... 71/77 |
| 2,706,151 | 4/1955 | Clarke et al. ........................... 71/77 |
| 2,989,821 | 6/1961 | Blondheim et al. ..................... 47/1 |
| 3,131,059 | 5/1964 | Hoffman ................................. 47/1 |
| 3,564,768 | 2/1971 | Hoffman ............................. 47/57.6 |
| 3,598,565 | 8/1971 | Graves ................................... 71/77 |
| 3,617,247 | 11/1971 | Chiles, Jr. ............................. 71/77 |
| 3,674,458 | 7/1972 | Schattner .............................. 71/77 |
| 3,698,133 | 10/1972 | Schreiber ............................ 47/57.6 |
| 3,703,404 | 11/1972 | Kirk ..................................... 117/72 |
| 3,707,807 | 1/1973 | Graves ............................... 47/57.6 |
| 3,728,099 | 4/1973 | Chiles, Jr. ............................. 71/77 |
| 3,803,761 | 4/1974 | Watts et al. ............................ 71/77 |
| 3,808,740 | 5/1974 | Porter et al. ........................ 47/56.6 |

FOREIGN PATENT DOCUMENTS 159917  3/1953  Australia ................................. 71/77

OTHER PUBLICATIONS

Dobozy et al., Tenside Detergents, vol. 13 (1976), p. 3.
Heydecker et al., Nature, vol. 246 (1973), pp. 42–44.
Swisher, "Surfactant Biodegradation", Marcel Dekker, Inc., New York, 1970.
Swisher, "Archives of Environmental Health", vol. 17 (1968), pp. 232–246.
Toxic Substances List, 1973 Edition, U.S. Dept. of Health, Education and Welfare, Rockville, Md.
Ernst et al., American Orchid Society Bulletin, vol. 39 (1970), pp. 599–605.
Park Seed Catalog, Geo. W. Park Seed Co. Inc., Greenwood, S.C. (1974–1975).
Ernst et al., New Phytol, vol. 70 (1971), pp. 457–482.
Arditti et al., American Orchid Society Bulletin, vol. 40 (1971), pp. 317–318.
Boodley et al., "Cornell Peat-Lite Mixes for Commercial Plant Growing", Cornell University, Ithaca, New York.
Article in London Sunday Times, Dec. 15, 1974, Describing Heydecker'S work.
The Gardener's Handbook, Geo. W. Park Seed Co., Greenwood, S.C.
"Selecting and Growing House Plants", U.S.D.A. Home and Garden Bulletin No. 82, Washington, D.C. (1968).
Endo et al., Agron. J., vol. 61 (6) (1969), pp. 850–854.
Kale et al., Indian J. Agrio. Sci., vol. 38, (1968), pp. 504–512.
Hartmann, Gas-Wasser Fach., vol. 107 (10), (1966), pp. 251–255.
Kawamura et al., Chem. Phys. Appl. Surface Active Subst. Proc. Inst. Congr (4th) 1967, Gordon Breach Sci. Publ., London.
Itoh et al., Biochem. Biophys. Acta, vol. 69 (1963), pp. 130–142.
Rotini et al., Ricerca Sic. Rend., vol. 1, (1961), pp. 30–36.
Kuiper, Meded. Landbouwhogesch. Wageningen (1967), p. 23.
Fumridge, J. Sci. Food Agr. 10 (1959), pp. 419–425.
Goldhammer, Nature, vol. 178 (1956), pp. 1286–1287.
Parr et al., Botan. Gaz., vol. 127 (2) (1965), pp. 86–96.
Goldberg, Riv. Ital. Sostaze Grasse, vol. 45(2), (1968), pp. 108–115.

*Primary Examiner*—Catherine L. Mills
*Attorney, Agent, or Firm*—James J. Farrell; Melvin H. Kurtz; Ira J. Schultz

[57] ABSTRACT

A method of treating seeds after they are sown to increase the rate and/or yield of germination is disclosed together with surfactant compositions which will accomplish such favorable germination. The surfactants used must generally not accumulate in the root tissue or in the environment; they must be substantive to root tissue of the seedling as it forms until the surfactant degrades. The surfactants must also be nontoxic at levels employed and must not readily react with hardness ions, such as calcium or magnesium in order to maintain their efficacy in the soil.

2 Claims, No Drawings

METHOD FOR INCREASING THE RATE AND/OR YIELD OF SEED GERMINATION BY TREATMENT WITH SURFACTANTS

This invention broadly relates to the use of surfactants on plant seeds that normally take more than about 5 days to germinate, to increase both the rate and yield of seed germination.

Improved yield and/or rate of plant seed germination is especially valuable in the areas of commercial grain crops, vegetables, fruits, lumber crops, fibers, nursery crops, both commercial and home grass growing, home fruit and vegetable growing and home flower cultivation. All of these areas would realize substantial benefits from an increase in the rate and yield of seed germination. Generally, growing plants such as commercial vegetable or grain crops as well as trees for lumber and fruit crops, depend for their growth on the vagaries of weather conditions, fertility of the soil, moisture availability and the like. If the number of seeds planted were to be increased, the cost of planting the seeds would, of course, increase accordingly. In many species of plants the rate of seed germination is very slow and the actual yield of seed germination is also very low. Thus, an effective treatment which would cause an increased yield at an increased rate of seed germination is seen to be extremely desirable.

Surfactants have been used in conjunction with plants for many purposes. Australian Patent No. 159,917 to Goldhammer deals mainly with spraying fruit or plants with surfactant solutions to preserve freshness. Very high concentrations of the surfactant are utilized and several of the Examples in the patent relate to the treatment of seeds, many seeds were soaked in solutions of varying surfactants. The plants are then grown on cotton wool and the subsequent fate of the plants was not determined. It is thus not indicated in this patent whether the plants grew to be normal healthy plants but any increase in the rate and/or yield of seed germination to be acceptable, must of necessity, result in the production of healthy plants. The teaching of this patent is doubtful based on an article in "Nature" written some four years after the issuance of the patent by the patentee, i.e. Goldhammer, "Nature", 178 (1956) pp. 1286-1287. The article indicates that nonionic surfactants cause a speeding up of metabolic processes in living plants. The article also indicates that distortion of flowering often results and that it is not known whether these compounds have growth regulating properties. Additionally, in an article by Walter Heydecker et al in "Nature", 246 (1973) pp. 42-44, the use of polyethylene glycol (PEG) of relatively high molecular weight (Carbowax 6000) for treating seeds is disclosed. The polyethylene glycol in this article was utilized to pretreat seeds from 3 to 23 days by placing them on paper moistened with the polyethylene glycol solution. The author states that the mechanism is an osmotic treatment and that the solutions control the amount of water that will be transported into the seed. According to the article, after treatment the seeds can be stored and then when planted germinate more quickly. This procedure necessitates a pretreatment and is not applied as part of the usual watering of seeds after they are sown. In addition, polyethylene glycol is not biodegradable by many of the usual criteria, and would not be preferred for environmental use.

Many other articles are available with respect to the use of surfactant treatment of plants and many U.S. patents have issued containing references to surfactants in conjunction with plants. However, the art is confused with respect to the use of surfactants with plants and does not appear to specifically recommend their utilization. This can be observed from articles by Ernst et al in the "American Orchid Society Bulletin", Volume 39, (1970), pp. 559-605 and in "The New Phytologist", Volume 70, (1971), pp. 457-482. In these papers it is concluded that ionic surfactants used above 100 ppm (parts per million) were damaging to orchid seedlings but that larger percentages of seedlings survived at higher application levels, for example, up to 1000 ppm. The authors, based on these experiments and other reported work, concluded that surfactant toxicity is due to possible emulsification of membrane lipids as well as precipitation and dispersion of cellular proteins. It was noted that one of the surfactants used lauroyl/myristoyl di(2-hydroxymethyl)amide brought about retardation and killing even though structural effects in the seeds were not noted. In addition, several common books on gardening recommend soaking the soil (referred to variously as compost, potting media, and the like) with water before using and actually immersing plants, to water them, because "lack of wetting" can be a problem anytime after the soil dries out. Several books also include mention of "wick" watering or subirrigation to avoid the "lack of wetting" problem. Examples of these are in "The Gardener's Handbook" available from George W. Park Seed Company, Greenwood, South Carolina and "Selecting and Growing House Plants", U.S. Department of Agriculture Home and Garden Bulletin No. 82, Washington, D.C. (1968). A Cornell University Bulletin by James W. Boodley, et al entitled "Cornell Peat Light Mixes for Commercial Plant Growing", Cornell University, Ithica, New York, lists some nine (9) surfactants for the purpose of wetting soil. Several articles, in addition, list damaging effects of certain nonionic surfactants, see for example "Effects of Nonionic Surfactants on Monocots" by Endo et al in the Journal of Agronomy, Volume 61(6), (1969) pp. 850-854.

The premise that surfactants damage plants runs through many papers. Significant damage to radishes is reported at concentrations as low as 25 parts per million of alkylbenzene sulfonate while Okra survived a concentration up to 50 parts per million. This was reported by Kole et al in the "Indian Journal of Agriculture Science", Volume 38, (1968), pp. 504-512. This premise also appears to be held in articles by Hartman in Gas-Wasserfach, 107 (10) (1966), pp. 251-255 and Kawamura et al in "Chem. Phys. Appl. Surface Active Subst. Proc. Inst. Congr.", 4th (1964) published in 1967 by Gordon Breach Scientific Publications, London. It is thus evident that the use of surfactants in conjunction with plants in at best confused. As previously stated, it would be highly desirable to find a method for increasing the rate and/or yield of germination of seedlings. Increased rate and/or yield of seed germination is made possible through utilization of applicant's invention by a post sowing treatment of selected plant seeds, which require more than about 5 days to germinate, with an aqueous solution or dispersion of a selected growth increasing surfactant.

The treatment is applied after sowing along with the normal watering of the seeds. The surfactant to be used is either dissolved or dispersed in an aqueous solution and then applied in appropriate concentrations to the soil in which the seeds have been planted.

The amount of surfactant used to prepare the watering solution is about 100 ppm (parts per million) to about 1000 ppm. Some of the surfactants used may not form a true solution but rather may be in the form of a dispersion. The term "solution" will be used hereinafter for convenience to mean either solution or dispersion. The exact concentration of solute or dispersed surfactant in solution is not critical so long as the seed is treated with an amount effective to increase its germination rate and/or yield.

The surfactants that can be used must meet several criteria as follows:

(a) not accumulate in the root tissue or the environment (i.e. be rapidly biodegradable)

(b) be substantive to root tissue of the seedling as it forms until the surfactant degrades (c) surprisingly the surfactants, although used on plants, must be non-toxic at levels used assuming a toxicity criteria such as acute animal toxicity (d) not reach readily with hardness ions such as calcium or magnesium in order to maintain efficacy in soil.

The biodegradability and acute oral toxicity in rats of several selected surfactants is reported in Table I. The biodegradability data is taken from R. D. Swisher, "Surfactant Biodegradation", Marcel Dekker, Inc., New York, 1970. The toxicological data is taken from an article by R. D. Swisher in the Archives of Environmental Health 17 (1968) pp. 232-246.

TABLE 1

| SURFACTANT BIODEGRADATION AND TOXICITY | | |
|---|---|---|
| Item | Extent of Biodegradation | Acute Toxicity (Rat Oral $LD_{50}$) mg/kg |
| PEG 6000 | 0 | — |
| Triton X-100 | 59[i] | ~1,600 |
| LAS | 86[ii] | 1,260,650 |
| | 63-80[iii] | |
| Lauryl alcohol (3 E.O.) sulfates | ~90% | 1,820 |
| Oleoyl methyl tauride | ~50, 100, 100[iv] | 4,000+ |
| Lauryl alcohol (7E.O.) | 96-100 | 4,150 |
| Stearyl alcohol (2E.O.) | ~100 | 25,000+ |
| Stearyl alcohol (10E.O.) | 74, 70, 100 | 2,900 |
| Stearyl alcohol (20 E.O.) | 7, 32, 100 | 1,900 |

[i]mean of 28 values
[ii]mean of over 50 values for $C_{12}$ LAS
[iii]value given for commercial LAS
[iv]based on taurine Since the biodegradability data are not precise, the acute toxicity data must be relied on as a primary condition modified by biodegradability. The acute toxicity criteria is thus the predominant condition. Both low toxicity and high biodegradability are desired but acceptable biodegradability alone will not overcome increased toxicity. If lauryl alcohol (3 E.O.) sulfate is taken as the cut-off criteria, compounds with higher $LD_{50}$'s and not much lower extents of biodegradating should be considered. Thus longer chain alcohol (E.O.) sulfates are preferable; nonionics with $C_{12}$ and up carbon chains but not more than about 9-10 moles of E.O. per mole of alcohol are suitable as well as the longer chain taurides. High E.O. contents and short chains should be avoided.

The surfactants that can be used, keeping in mind the above criteria, are long chain alcohol E.O. sulfates

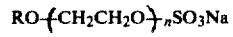

where R is $C_{12}$ to $C_{18}$ and n is no greater than about 9 to 10.

Long Chain Acyl Taurides

wherein R is $C_{14}$ to $C_{20}$ such as, for example tallow.

Long Chain Ethoxylated Alcohols

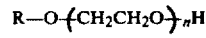

where R is $C_{14}$ to $C_{20}$ and n is no greater than about 9 to 10.

Long Chain Acyl Isethionates

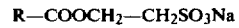

where R is $C_{12}$ to $C_{20}$.

The types of seeds that can benefit from application of the invention range from flowers and grasses to commercial crops such as peas and onions and trees such as Norway spruce. Thus the seeds that the invention is applicable to are, for example, those from the family Liliaceae, legume of the family Fabaceae, flowers from the family Compositae, labiatae and geraneaciae, lawn grasses and range grasses, and trees of the order coniferae.

A number of surfactants were employed for use in experiments. These surfactants and the abbreviations used in the Examples are set out in Table II following.

TABLE II

SURFACTANTS USED IN EXAMPLES

L = LAS linear alkylbenzene sulfonate having principally $C_{10}$–$C_{15}$ in the alkyl chain.
LI = Lauroyl Igepon T[1] $C_{11}H_{23}CON(CH_3)C_2H_4SO_3Na$
TI = Tallow Igepon T[1] R—$CON(CH_3)C_2H_4SO_3Na$ where RCO— is a mixture of the acid residues of tallow. Tallow has the following formula:
     2–3% myristic acid,
     24–32% palmitic acid,
     14–32% stearic acid,
     1–3% palmitic acid,
     35–48% oleic acid, and
     2–4% linoleic acid.
LIA = Lauroyl Igepon A[1] $C_{11}H_{23}COOCH_2CH_2SO_3Na$
N = Neodol 45-7[2] $RO(CH_2CH_2O)_nH$ where R averages $C_{14}$ to $C_{15}$ and n is 7.
B = Neodol 3 E.O. Sulfate[2] $RO(CH_2CH_2O)_nSO_3Na$ where R averages $C_{14}$ to $C_{15}$ and n is 3.
PEG = Polyethylene Glycol (Carbowax 6000)[4] $HOCH_2CH_2O(CH_2CH_2O)_xH$ where x is sufficient to produce an average molecular

TABLE II-continued
SURFACTANTS USED IN EXAMPLES weight of 6000 to 7500

Neodol 49-7[2] RO+CH$_2$CH$_2$O+$_n$ where R = C$_{14}$-C$_{19}$ and n = 7

Triton X-100[3] octylphenoxy polyethoxy ethanol

Lauryl alcohol 3 E.O. sulfate RO+CH$_2$CH$_2$O+$_n$SO$_3$Na where R is 12 and n is 3.

Lauryl alcohol 7 E.O. sulfate RO+CH$_2$CH$_2$O+$_n$SO$_3$Na where R is 12 and n is 7.

Stearyl alcohol 2 E.O. sulfate RO+CH$_2$CH$_2$O+$_n$SO$_3$Na where R is 18 and n is 2.

Stearyl alcohol 10 E.O. sulfate RO+CH$_2$CH$_2$O+$_n$SO$_3$Na where R is 18 and n is 10.

Stearyl alcohol 20 E.O. sulfate RO+CH$_2$CH$_2$O+$_n$SO$_3$Na where R is 18 and n is 20.

Oleyl methyl tauride[1] C$_{17}$H$_{33}$CON(CH$_3$)C$_2$H$_4$SO$_3$Na

[1] a product marketed by GAF Corporation.
[2] a product marketed by Shell Chemical Company.
[3] a product marketed by Rohm & Haas Company.
[4] a product marketed by Union Carbide Company.

The following Examples will more fully illustrate the embodiments of this invention. All parts, percentages and proportions referred to herein and in the appended claims are by weight unless otherwise indicated.

In all of the experiments germination rate and yield were measured from actual soil preparations. Parks' Sowing Mix was used in all experiments to maintain the soil as a constant. This mix is sold by Park Seed Company, Greenwood, South Carolina, and is pre-packaged including fertilizer. This also eliminates any effect that the surfactants might have as a food source as they biodegrade.

All experiments were performed using 8 oz. (236.6 cc) plastic containers. A measured amount of 125 cc of the sowing mix is placed in the containers and leveled by shaking the container. The seeds are sown and the containers initially "watered" with 80 ml of the test or control solutions. The number of seeds per container is made identical where possible and both a water and negative control scheme are used. The negative controls selected were LAS and Lauroyl Igepon T both anticipated as giving harmful results from the literature. The test solutions were made up to the required concentration (either 1000 ppm or 100 ppm in the experiments) as needed.

All except the initial experiment were performed in a constant humidity (70% RH)/constant temperature room with 16 hours of light Humidity and light were thus removed as variables. The conditions maintained in this room are conducive to germination of most seeds. Thus, positive effects under these conditions are particularly meaningful. Under adverse conditions it is likely that the results could be much greater than those recorded in the Examples herein.

After the initial watering with the test solutions, the seeds are watered only with plain water as needed. In the case of very recalcitrant seeds the surfactant treatment was repeated once or twice more spaced by regular watering. In most cases the single treatment scheme was used.

The day of germination and a record of numbers of plants germinated versus time were kept as a means of determining rate and yield. After the experiments, samples from the experimental batches were kept to insure that the plants grew normally and to maturity.

The data was analyzed using the $X^2$-test to distinguish whether there was a difference between treatments and/or between any two individual treatments. In one case (Example IX) a factorial designed experiment was run to study several effects (treatments, concentrations of surfactant, time) at once.

EXAMPLE I

A hybrid *Coleus Dwarf Salicifolius* was selected because the germination time was given as 10 days and seeds from identical lots prepared in identical packets (40 seeds/packets) were obtainable. It is also known to grow uniformly to a height of 8–10 inches and thus provides a good model. Six containers with soil were prepared and 40 seeds per container put in. One container was watered with water alone and two others were watered with 1000 ppm solutions of Linear Alkylbenzene Sulfonate (LAS) and Lauroyl Igepon T. These were the negative controls (i.e. give a negative effect). Neodol (3 E.O.) Sulfate, Neodol 45-7 and Tallow Igepon T were selected to provide a positive effect and were also used at 1000 ppm.

40 Seeds of *Coleus Dwarf Salicifolius* were placed in each container:

| Treatment | Number of Seedlings After | |
|---|---|---|
| | 6 Days | 16 Days |
| Water | 19 | 17 |
| L | 31* | 0 |
| LI | 30* | 0 |
| B | 33 | 29 |
| N | 33 | 32 |
| TI | 40 | 33 |

*Small and spindling seedlings

The average germination time for Coleus is around 10 days (2) so it can be seen that after 6 days there was an enhancement in rate and after germination was completed an enhancement in yield (after 16 days).

In the above experiment statistical analysis shows that after both times the treatments are different at the 99.5% confidence level or greater ($X^2 = 33.54$). At the six day mark all treatments are significantly different than the control at the 97.5% confidence level (i.e. $X^2$ for nearest value = 5.59). Significance at day 16 is much greater.

The experiment gave the surprising result that 29–33 healthy seedlings came from the containers treated with the selected surfactants compared to 17 for water alone and none from LAS and Lauroyl Igepon T. In the case of the negative control surfactants the seedlings germinated in greater numbers but subsequently shriveled and died never reaching a healthy state.

EXAMPLE II

Soybeans "Edible" "Pickett" showed no differences in germination between the controls and anticipated beneficial surfactants. It should be noted that this item germinates very readily and completely. Seeds which germinate readily and completely do not need the treatment of the invention. Readily and completely based on the experience gained in these experiments is defined as a high germination yield within 5 days.

20 seeds of the Soybeans were added to each container. 1000 ppm (parts per million) of surfactants was used on each.

| Treatment | Number of Seedlings After | |
|---|---|---|
| | 8 Days | 15 Days |
| Water | 7 | 12 |
| N | 2 | 10 |
| TI | 3 | 7 |
| L | 5 | 9 |
| B | 5 | 13 |
| LI | 0 | 4 |

This experiment was also run with additional treatments of water and surfactant to determine phytotoxicity due to accumulation. The plants were treated once a day with the water/surfactant solution. Results are as follows:

| Treatment | Number of Seedlings After | |
|---|---|---|
| | 9 Days | 14 Days |
| Water | 14 | 17 |
| TI | 9 | 12 |
| B | 14 | 14 |
| N | 11 | 12 |
| LI | 0 | 0 |
| L | 8 | 12 |

EXAMPLE III 20 seeds each of Wrinkled Peas, Laxton's Progress were used in each container. 100 ppm of surfactant was used.

| Treatment | Number of Seedings After | | |
|---|---|---|---|
| | 4 Days | 6 Days | 25 Days |
| Water | 2 | 3 | 11 |
| L | 13 | 14 | 9 |
| TI | 17 | 18 | 18 |
| N | 11 | 14 | 15 |
| B | 6 | 11 | 13 |

The LAS seedlings are noticeably less healthy than the others, the seedlings are spindly and the leaves are smaller. The peas, however, seem to be able to survive the toxicity of LAS to a better degree than other plants. The results of this experiment are highly significant in showing a great benefit for Tallow Igepon T. 90% of the Tallow Igepon T treated seeds germinated after 6 days compared to a total of 55% in the control even after 25 days. The Neodol 45-7 and Neodol 3 E.O. sulfate will also be seen to be useable on various seeds as would be expected.

EXAMPLE IV 40 seeds of Onion Crystal Wax (White Bermuda) were placed in each container. 100 ppm of surfactant was used.

| Treatment | Number of Seedlings After | | |
|---|---|---|---|
| | 8 Days | 11 Days | 15 Days |
| Water | 5 | 11 | 14 |
| TI | 11 | 16 | 17 |
| N | 6 | 7 | 7 |
| B | 2 | 5 | 5 |
| LI | 0 | 0 | 0 |
| L | 0 | 0 | 0 |

After 8 days the $X^2$ value is 17 indicating a confidence level of 99.5% in the difference between treatments. The Tallow Igepon T is better than the control after 8 days at the 90% confidence level.

EXAMPLE V 100 seeds of Fylking Kentucky Bluegrass were placed in each container. 1000 ppm of surfactant was used.

| Treatment | Number of Seedlings After | | | |
|---|---|---|---|---|
| | 6 Days | 8 Days | 10 Days | 13 Days |
| Water | 4 | 11 | 12 | 18 |
| N | 16 | 24 | 32 | 33 |
| B | 13 | 35 | 46 | 55 |
| TI | 10 | 25 | 37 | 38 |
| L | 2 | 7 | 11 | 8 |
| LI | 1 | 4 | 8 | 8 |

All of the three preferred surfactants are highly significant in their effects on improving both the rate and yield of Bluegrass.

EXAMPLE VI 50 seeds each of *Helianthus Giganteus* (Sunflower) were placed in each container. These seeds reportedly germinate in 5 days or less so one would not anticipate any benefit from this treatment. 1000 ppm of surfactant was used.

| Treatment | Number of Seedlings After 5 Days |
|---|---|
| Water | 44 |
| L | 27 |
| N | 50 |
| TI | 45 |
| B | 34 |

The differences between treatments overall is highly significant (>99.5% confidence, $X^2=43.25$) because of the negative effect of LAS. Statistically, the Neodol 3 E.O. sulfate result is just significant at the 97.5% confidence level compared to the control. The "benefit" due to the nonionic (N) is also significant at this level ($X^2=6.38$). However, due to the difficulty in interpreting results for the rapidly germinating seeds, more replicates would be necessary to determine whether the statistically significant results in this experiment could be reproduced. This example clearly shows the negative aspects of using the incorrect surfactant in a process of this type.

EXAMPLE VII 30 seeds each of Pelargonium (Geranium) Nittany Lion were placed in each container. Geraniums are a particularly awkward plant to grow from seed because the germination time is long (ca. 30 days) and it is also known that certain of the seeds can lie dormant for even much longer periods, i.e. there is a lack of uniformity in germination between seeds from the same variety. This makes the data very difficult to interpret. 1000 ppm of surfactant was used.

| Treatment | Number of Seedlings After | |
|---|---|---|
| | 8 Days | 11 Days |
| Water | 2 | 2 |
| LI | 1 | 1 |
| L | 2 | 2 |
| TI | 3 | 5 |
| N | 7 | 7 |
| B | 2 | 2 |

This experiment was not followed through to completion but after 11 days there is a difference in treatments which is significant at slightly over the 90% confidence level with the two favored surfactants showing promise. (The Neodol 45-7 treatment is significantly different than water at greater than 90% confidence.) A later attempt to repeat the experiment on Geranium was thwarted by fungus infestation that killed many of the germinating seedlings thus ruining the experiment.

This brings up an interesting observation that was made during the course of the experiments. It was noted that a fine green "fuzz" coated the surface occasionally after a few days of growing for the controls but did not exist on the surfactant treated containers (at least not during the time spans over which the experiments were carried out). Microscopic examination identified the material as lichen. Presumably the surfactant acts to interrupt the extracellular transport mechanism between the fungi and algae that go into making the lichen because the surfactants in question are not known to be effective algacides or fungicides.

EXAMPLE VIII

A series of containers were sown with *Picea Abies* (Norway Spruce) as an attempt to study the "woody" family of plants. They are similar to other pines in that cold is considered necessary for their germination. The usual procedure is either to refrigerate before planting or plant in the fall for spring germination. Such techniques are also recommended for other hardy ornamental plants such as Azalea. Thus, several months were anticipated for germination if at all. 75 seeds were sown in all containers except for the TI container where only 62 seeds remained from the packets purchased.

| Treatment | Number of Seedlings After | | | |
|---|---|---|---|---|
| | 10 Days | 16 Days | 21 Days | 32 Days |
| Water | 0 | 7 | 12 | 8 |
| N | 1 | 6 | 10 | 9 |
| TI | 1 | 9 | 16 | 14 |
| L | 0 | 0 | 0 | 0 |
| LI | 0 | 0 | 0 | 6 |
| B | 0 | 1 | 2 | 2 |

It was noted throughout the experiment that many of the seedlings germinated and then died. The numbers shown above do not include seeds which germinated and then died which accounts for the difference between 32 days and 21 days. While the conditions used for the experiments are ideal for algae and fungal growth so that the seedlings in all of the experiments are subject to this hazard. In this experiment the 32 day value for the Tallow Igepon T treatment is significantly better than water at well above the 90% confidence level and just below 95% confidence.

EXAMPLE IX

A second test, similar to Example I, was run to establish reproducibility of the results. Also of interest was a determination of the effect of level of use of the surfactants. Additionally, it was desired to study the effect of a humectant material such as PEG since although not considered a surfactant it was used by Heydecker et al as part of their osmotic control work.

An attempt was made to obtain the same seeds as obtained earlier and it was found possible to obtain *Dwarf Coleus Saliciflorius* seeds from the same source. The type (genus) is the same but the crop and exact nature of the hybrid are probably somewhat different because these were called "Red Shades."

The seeds were sown 40 to a container and the following treatments were utilized:

| Code | Treatment |
|---|---|
| C | Water control |
| L | LAS negative effect control using 1000 ppm LAS solution |
| PEGHI | Initial watering made with a 1% soluton of Polyethylene Glycol (Carbowax 6000) |
| PEGLO | Initial watering with 1000 ppm of Carbowax 6000 |
| NHI | Initial watering with 1000 ppm of Neodol 45-7 |
| NLO | Initial watering with 200 ppm of Neodol 45-7 |
| TIHI | Initial watering with 1000 ppm of Tallow Igepon T |
| TILO | Initial watering with 200 ppm of Tallow Igepon T |
| LIAHI | Initial watering with 1000 ppm of Lauroyl Igepon A |
| LIALO | Initial watering with 200 ppm of Lauroyl Igepon A |

This experiment could be analyzed using $X^2$ statistic but it was so designed that after making sure that the experiment was valid by comparison to the positive and negative controls it could be analyzed by analysis of variance since the last 8 conditions represent a design with 4 treatments at two levels of concentration. By recording the numbers of seedlings as a function of time, time can also be introduced as a variable. The data is as follows:

| Treatment | Number of Seedlings After | | | |
|---|---|---|---|---|
| | 7 Days | 8 Days | 11 Days | 13 Days |
| Water | 7 | 9 | 17 | 18 |
| L | 0 | 0 | 0 | 0 |
| PEGHI | 10 | 12 | 16 | 16 |
| PEGLO | 11 | 18 | 26 | 28 |
| NHI | 10 | 17 | 32 | 33 |
| NLO | 8 | 18 | 34 | 35 |
| TIHI | 7 | 13 | 32 | 33 |
| TILO | 15 | 22 | 37 | 37 |
| LIAHI | 4 | 11 | 15 | 16 |
| LIALO | 4 | 10 | 36 | 37 |

Using the analysis of variance approach on the last 8 sets one can conclude that TI and N are statistically equivalent and significantly better than LIA and PEG overall. Also, it is found that time and concentration do not interact with the treatments to a significant degree.

The difference between treatments, i.e. the compounds, is the biggest significant factor in the experiment.

Many interesting things came up with an analysis of individual parts of this experiment. For example, if the boxed results after 13 days are compared with the results at the completion of Experiment 1 the consistency is excellent. It is also apparent that 1000 ppm concentrations are not necessary. It is a good level since it appears to insure results but concentrations as low as 100 ppm look feasible. Experience with Alkyl Igepon A would indicate that homologs in this series should fit the model for a desirable surfactant since they are mild and readily biodegradable. The results of this experiment support this conclusion in that the Lauroyl Igepon A used here is not damaging at 1000 ppm and shows a positive effect at 200 ppm. In the other experiments Lauroyl Igepon T exhibited negative effects in all cases tested. Thus longer chain Igepon A derivatives should be even better and the hypothesis for selection of surfactants appears to hold. Exact $LD_{50}$ data for Lauroyl Igepon A are not available but a closely related compound (one methyl group difference) is known to have an $LD_{50}$ of 3300 mg/kg (37) which fits into the scheme quite well.

Additional experiments were run as follows:

*Kalmia Latifolia* (Mountain Laurel) which has a long germination time showed some response to surfactant treatment (approximately 25 germinations to 15 for the control out of 200 or so extremely fine seeds planted).

A single instance of germination of *Rhododendron Ferrugineum* from surfactant treatment was recorded a few days after an unknown quantity of seeds were planted. Rhododendron are extremely difficult to grow from seeds.

*Zoysia Japonica* experiments show some effect for surfactant treatment compared to no results whatsoever for the control group.

The Examples clearly indicate that it is possible to achieve beneficial effects on germination rate and yield of seeds which require more than approximately five days to germinate. The surfactants of choice are those which are mild by animal toxicity criteria. The exact degree of "mildness" required is dependent on the sensitivity of the plant but the rank order holds. The acute toxicity data appears to be a better guide than biodegradability although the latter is important from a utility point of view, i.e. one would not wish to use such a process commercially with non-biodegradable surfactants. The concentration required is in the range of 100 to 1000 ppm.

In view of the preceeding description and Examples, various modifications thereof will be suggested to those skilled in the art and are to be included within the spirit and purview of this application and the scope of the appended claims.

What is claimed is:

1. A method of increasing the germination rate and germination yield of plant seeds normally requiring substantially more than about 5 days to germinate comprising: treating said seeds after planting with an aqueous solution containing about 100 to about 1000 parts per million of a growth increasing surfactant selected from the group consisting of:

(a) long chain alcohol ethoxylate sulfates of the formula

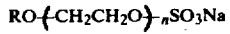

where R is about $C_{12}$ to $C_{18}$ and n is no greater than about 9 to 10;

(b) long chain acyl taurides of the formula

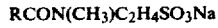

where R is about $C_{14}$ to $C_{20}$; and (c) long chain ethoxylated alcohols of the formula

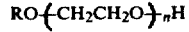

where R is about $C_{14}$ to $C_{20}$ and n is no greater than about 9 to 10.

2. A method of increasing the germination rate and germination yield of plant seeds normally requiring substantially more than about 5 days to germinate, comprising: treating said seeds after planting with an aqueous solution containing about 100 to about 300 parts per million of a growth increasing sufactant selected from the group consisting of long chain acyl isethionates of the formula

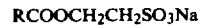

where RCO is about $C_{12}$ to C20.

* * * * *